United States Patent [19]

Hurd

[11] 4,367,767
[45] Jan. 11, 1983

[54] SERVO-CONTROLLED GAS PRESSURE RELIEF VALVE

[75] Inventor: Claude C. Hurd, Riverside, Calif.

[73] Assignee: Bear Medical Systems, Inc., Riverside, Calif.

[21] Appl. No.: 212,889

[22] Filed: Dec. 4, 1980

[51] Int. Cl.³ .............................................. F16K 17/10
[52] U.S. Cl. .................................. 137/489; 137/492.5
[58] Field of Search ................ 137/489, 491; 251/45; 137/492, 492.5

[56] References Cited

U.S. PATENT DOCUMENTS

| | | | |
|---|---|---|---|
| 2,416,855 | 3/1947 | St. Clair | 137/53 |
| 2,737,974 | 3/1956 | Renick | 137/489 |
| 2,904,035 | 9/1959 | Andreasen | 128/29 |
| 3,036,778 | 5/1962 | Dillman | 236/80 |
| 3,461,908 | 8/1969 | Newcomb et al. | 137/492.5 |
| 3,545,887 | 12/1970 | Kobnick | 417/307 |
| 3,578,018 | 5/1971 | Dillon | 137/491 X |
| 3,648,716 | 4/1972 | Joesting | 137/85 |
| 3,662,779 | 5/1972 | Weber et al. | 137/489 |
| 4,058,287 | 11/1977 | Fromfield | 251/46 |
| 4,151,856 | 5/1979 | Burrus | 137/84 |

FOREIGN PATENT DOCUMENTS

| | | | |
|---|---|---|---|
| 528586 | 7/1950 | Canada | 137/491 |
| 1360867 | 4/1964 | France | 137/491 |

*Primary Examiner*—Alan Cohan
*Attorney, Agent, or Firm*—Howard J. Klein

[57] ABSTRACT

A servo-type gas pressure relief valve for regulating air pump pressure to pneumatic components of a medical ventilator or similar equipment utilizes a small diaphragm-type bleed or pilot valve to control the action of a main diaphragm valve. A small amount of inlet gas from the bottom side of the large diaphragm is passed through a restricted orifice to the top side of the large diaphragm. The bleed valve bleeds this gas to the atmosphere at a selected pressure, said bleeding action creating a pressure differential across the diaphragm of the main valve, which is thereby opened to exhaust gas to the atmosphere. A screw adjustment exerts tension on a spring which, in turn, exerts a force on the upper part of the bleed valve diaphragm. By adjusting the tension on the spring, the pressure at which air is bled to the atmosphere can be controlled, thereby accurately controlling the pressure at which the main valve opens.

8 Claims, 2 Drawing Figures

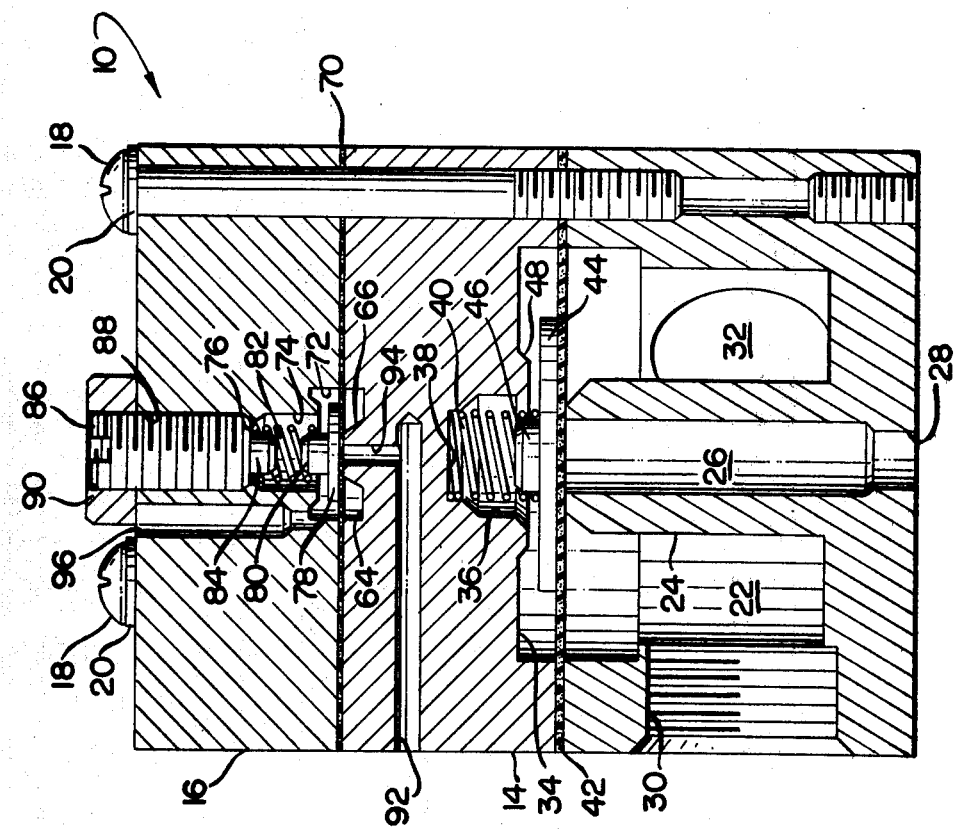
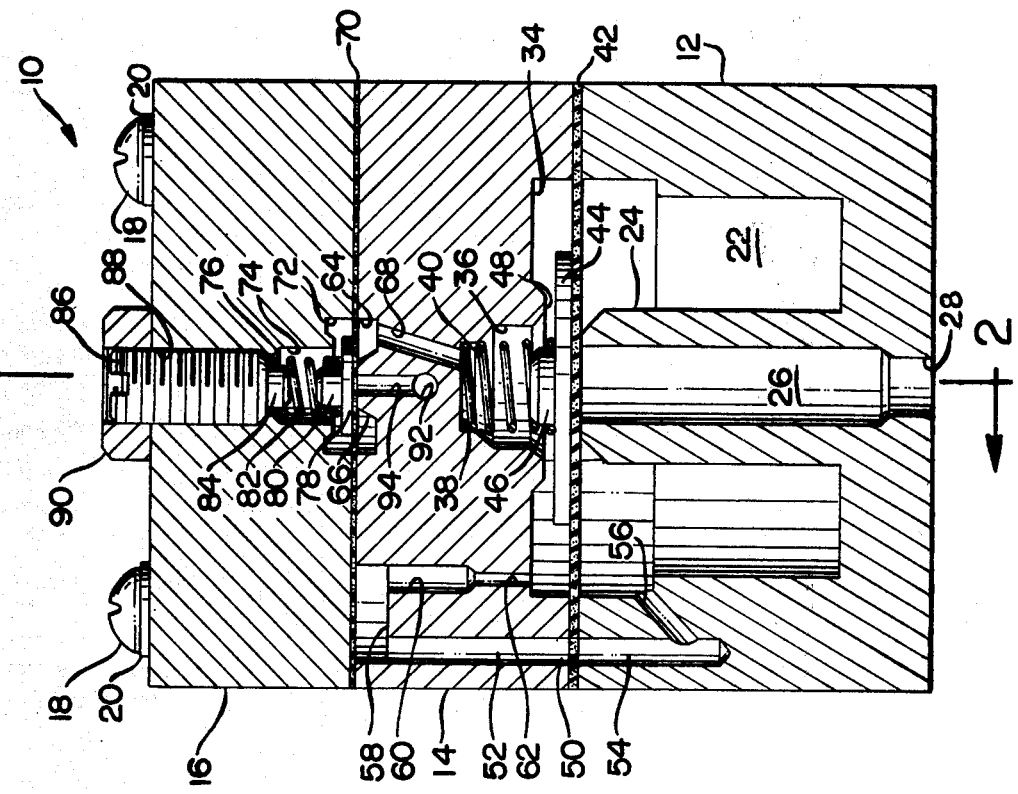

SERVO-CONTROLLED GAS PRESSURE RELIEF VALVE

BACKGROUND OF THE INVENTION

This invention relates to the field of gas pressure relief valves, and, in particular, it relates to a gas pressure relief valve for use between a gas pump or compressor and pneumatic components of a medical ventilator or similar equipment, whereby the pressure delivered to the pneumatic components remains substantially constant throughout a wide range of gas flow rates.

Typically, overpressure relief in a pneumatic system employing an air or gas compressor is provided by a poppet-type valve, which is spring-biased to open when a preselected pressure is exceeded. While in many applications a poppet-type valve achieves satisfactory results, the inherent limitations in poppet-type valves make them less than optimal for use in certain other applications. Specifically, poppet valves are usually operable in only a relatively narrow flow rate range without the introduction of relatively large pressure changes in the system due to the increasing force applied by the bias spring as the valve opens more widely to accommodate increasing flow rates. This factor may limit the utility of poppet valves in applications where precise pressure regulation is required over a wide range of fluid flow rates.

One particular application in which precise pressure regulation over a wide range of fluid flow rates is important is that of medical ventilators, used in assisting the breathing action of patients with pulmonary disabilities. Such devices typically employ an air compressor or pump to supply breathing gas (usually a variable mixture of air and pure oxygen) to a patient at flow rates which depend in large measure on the demands of the patient. These flow rates for a typical patient can range from near zero up to approximately 120 liters per minute (LPM). Moreover, such devices typically employ complex pneumatic components in controlling the flow of gas in accordance with the patient's needs. The accuracy and efficiency of such components can be increased, and their cost lowered, if the pressure supplied to them by the air compressor is precisely regulated so as to remain substantially constant, within close limits, over the full range of expected flow rates. Furthermore, constant pressure operation is desirable from the standpoint of the compressor, inasmuch as substantially constant load requirements allow the use of a smaller, and therefore less expensive, compressor than if varying loads are imposed.

Heretofore, in medical ventilators, overpressure relief between the compressor and the pneumatic components of the system has been achieved primarily by the use of poppet-type valves. See, for example, U.S. Pat. No. 3,756,229 to Ollivier. In order for such valves to perform acceptably over wide flow rate ranges, they must be carefully engineered, having, for example, springs specifically engineered (as to size, spring rate, etc.) to minimize, as much as possible, the effects of widely varying flow rates. Even so, variations from the nominal regulated pressure of 10 percent to 15 percent are typical for such valves when they are subjected to a flow rate range of 0 to 120 LPM.

Accordingly, a means has been sought for providing overpressure relief between the compressor and the pneumatic circuitry in devices such as medical ventilators wherein the aforementioned limitations imposed by poppet-type relief valves are avoided, or at least minimized, thereby allowing the delivery of a substantially constant gas pressure to the pneumatic circuitry over a wide range of flow rates.

SUMMARY OF THE INVENTION

The present invention comprises an overpressure relief valve which avoids the aforementioned disadvantages of poppet-type relief valves by employing a servo-type mechanism to actuate the valve in response to an overpressure situation. Broadly, the invention uses a small diaphragm-type pilot or bleed valve which is servo-actuated by sampling upstream pressure to control a large diaphragm valve which, in turn, allows the discharge of air to the atmosphere. The small diaphragm valve controls the pressure in an upper chamber which is between the two diaphragms. Air from the compressor is fed into a lower chamber which is situated between the large diaphragm and the bottom of the valve body. A small amount of air from this lower chamber is fed, via a restricted orifice, into the upper chamber, from which it is bled to the atmosphere by the opening of the pilot valve. This bleeding action causes a drop of pressure in the space above the large or main diaphragm (which space is in fluid communication with the upper chamber), so that the main diaphragm valve opens to allow the discharge of air to the atmosphere, thereby controlling the pressure within the lower chamber. Thus, air at a regulated pressure can be directed from an outlet in the lower chamber to the pneumatic components of the ventilator or like equipment.

In operation, a screw adjustment exerts a tension on a spring, which, in turn, exerts a force on the upper part of the pilot valve diaphragm. If, for example, the screw adjustment is loosened, the tension on the associated upper spring decreases, thereby decreasing the force on the upper portion of the upper diaphragm. The pressure on the bottom of the pilot valve diaphragm, from the air in the upper chamber, is bled out of the upper chamber to the atmosphere by the pilot valve. This causes the pressure in the upper chamber to decrease until the pressure on the bottom side of the pilot valve diaphragm is equal to the adjusted force of the aforementioned spring.

The decrease in pressure in the upper chamber reduces the pressure, as previously mentioned, on the upper side of the main diaphragm. Since the pressure on the bottom of the main diaphragm is now greater than the pressure on the top of the main diaphragm, the excess pressure in the lower chamber is dumped to the atmosphere, as mentioned above. Thus, the pressures in the upper and lower chambers become stabilized at substantially the same pressure.

It can therefore be seen that the screw adjustment controls the pressure at which the system is operating and determines the output pressure of the compressor.

The lower chamber is also provided with an outlet which feeds the pressure-regulated compressed gas to the pneumatic components which control the delivery of breathing gas to the patient. If the patient's demand for breathing gas decreases, the flow rate from the outlet will likewise decrease, and since the flow rate delivered to the lower chamber by the compressor remains constant, more gas will be vented to the atmosphere by the main valve to maintain the pressure within the lower chamber substantially constant.

In the case of spring-biased pressure regulation valves, it is well known to be desirable to minimize the amount of spring extension or compression required to open the valve. This is so because the force exerted by the spring, and therefore the pressure necessary to countervail the force of the spring, is proportional to the amount of spring extension or compression. Thus the regulated pressure will tend to increase from its nominal value by an amount proportional to the extent of spring extension or compression. Therefore, it can be seen that where precise pressure regulation is desired, such spring travel must be minimized.

In the present invention, it will be appreciated that the sampling orifice and the pilot valve diaphragm can be dimensioned and configured so as to achieve the bleeding function with a minimum amount of compression of the pilot valve bias spring. In the present design, this compression can be made to be very small over the entire range of contemplated flow rates, to the extent that deviations from the nominal regulated pressure can easily be reduced to less than five percent.

In addition, it will be seen that the spring tension adjustment screw allows fairly precise calibration and control of the nominal regulated pressure value.

Thus, it can be seen that the present invention provides precise pressure regulation over an extended flow rate range while allowing the compressor to run at a constant load. Moreover, these results are achieved with increased economy, accuracy, and efficiency as compared with poppet-type pressure regulation valves.

BRIEF DESCRIPTION OF THE DRAWINGS

FIG. 1 is a longitudinal sectional view of a gas pressure relief valve constructed in accordance with the present invention; and FIG. 2 is a longitudinal sectional view taken along line 2—2 of FIG. 1.

DETAILED DESCRIPTION OF THE INVENTION

STRUCTURE OF THE INVENTION

Although the present invention is described in the context of use with a medical ventilator, it will be appreciated that the invention is readily adaptable for use in other applications where the advantageous characteristics of the invention are desired. Many such adaptations and applications would be well within the abilities of those skilled in the appropriate arts, and are therefore to be considered within the scope of the present invention.

Referring to the drawings, a pressure relief valve constructed in accordance with the present invention is indicated generally by the numeral 10. The body of the valve 10 comprises three discrete sections: a bottom section or base 12, a middle section or cover 14 and a top section or lid 16. The three sections are held together by means such as screws 18 and lockwashers 20. The sections 12, 14, and 16 are advantageously, although not necessarily, cylindrical in shape, and may conveniently be of the same diameter so as to form a cylinder when the three sections are assembled. In the following discussion, it will be assumed that all three sections 12, 14, and 16 are circular in cross section.

The bottom section or base 12 is partially hollowed out to form a substantially annular lower chamber 22. The lower chamber 22 surrounds a central cylinder 24, which is axially bored through to form a conduit 26 which, in turn, provides communication between the lower chamber 22 and the exterior of the valve 10 via an exhaust port 28 located in the bottom of the base 12. The top of the central cylinder 24 which contains the entrance to the conduit or bore 26 lies in or just slightly below a plane defined by the top of the base 12.

As shown in FIG. 2, the base 12 is provided with an inlet port 30 and an outlet port 32, both of which communicate with the lower chamber 22. The inlet port 30 is adapted for connection to a source of pressurized gas, such as an air pump or compressor (not shown). The outlet 32, in the case of a medical ventilator, is coupled with the pneumatic components and controls within the ventilator.

The bottom of the central section or cover 14 of the valve body is provided with a generally annular recess 34 surrounding a central axial bore 36 which extends approximately half way through the thickness of the cover element 14. The upper end of the bore 36 is necked down to a reduced diameter seat 38 which accommodates a main valve spring 40, as will be presently described.

Snugly engaged between the lower surface of the cover section 14 and the upper surface of the base section 12 is a main diaphragm 42, made from a thin sheet of resilient material, such as, for example, silicone-coated rayon. The diaphragm 42 isolates the space formed by the annular recess 34 from the chamber 22. Bonded to the top surface of the diaphragm 42, in the center thereof, is a circular main valve plate 44 having an upwardly extending axial boss 46 which seats the lower end of the main valve spring 40, the upper end of which is seated against the spring seat 38, as previously described.

The spring 40, the valve plate 44, and the diaphragm 42 together comprise the main exhaust valve assembly, with the upper end of the vertical cylinder 24 forming a valve seat during the operation of the valve, which will be described in detail later on. The spring 40 is preferably a highly compliant, lightweight spring which provides a stabilizing or damping function for the main exhaust valve, without imparting any significant amount of bias, other than that needed to maintain the valve lightly closed when the pressures on the two sides of the diaphragm 42 are substantially equal. The upward travel of the valve plate 44 is limited by an annular ridge 48 surrounding the opening of the bore 36.

As shown in FIG. 1, the annular space 34 above the diaphragm 42 is in fluid communication with the upper portion of the lower chamber 22 via a passage 50, the chamber 22 being otherwise isolated from the space 34 by the diaphragm 42. The major part of the passage 50 comprises a vertical bore 52 which extends through the entire thickness of the cover section 14. This bore 52 communicates, via an aperture (not shown) in the main diaphragm 42, with an aligned vertical bore 54 extending part way down through the thickness of the base section 12. The vertical bore 54 communicates with the chamber 22 via an angeled bore 56. The vertical bore 52 extends upwardly to the surface of the covered section 14, where it communicates with a horizontal passage 58, which may conveniently be formed by a circular recess in the top surface of the cover section 14. Situated radially inwardly of the bore 52 and extending downwardly from the horizontal passage 58 is another vertical bore 60 which advantageously extends approximately half way down into the cover section 14. The lower terminus of the passage leg 60 communicates with the annular space 34 via a restricted diameter orifice 62.

The top surface of the central or cover section 14 is provided with a small annular recess which forms an upper chamber 64, which surrounds an axial center projection 66, the purpose of which will be described hereinafter. The small upper chamber 64 communicates with the bore 36 via a passage 68 (FIG. 1).

Snugly held between the bottom surface of the top or lid section 16 and the top surface of the central or cover section 14 is a second, or "bleed" diaphragm 70. Centrally located in the bottom surface of the lid section 16 is a small annular recess 72, which forms a space to accommodate a bleed or pilot valve, as will be presently described. Extending upwardly from the space or recess 72 is an axial bore 74 having a necked-down upper terminus 76. Bonded to the center of the top surface of the diaphragm 70 is a circular bleed or pilot valve plate 78, having an upwardly-extending central boss 80 for carrying the lower end of a bleed valve spring 82. The spring 82 extends upwardly through the bore 72 with the upper end of the spring seated against a spring seat 84 carried on the bottom of an adjustment screw 86. The adjustment screw 86 (the purpose of which will be subsequently described) is retained in a threaded aperture 88 in the lid or top section 16 of the valve body, with the upper portion of the screw 86 projecting above the surface of the lid section 16 as shown. The screw 86 is used to adjust the tension on the spring 82, as will later be described in greater detail. Accordingly, retaining means such as a hex nut 90 may be used to lock the screw in the desired position.

The diaphragm 70, valve plate 78 and spring 82 together comprise a pilot valve or bleed valve, the purpose of which is to actuate the main valve assembly at a specified pressure, as will be described later on. As shown in the drawings, the projection 66 in the center of the annular recess 64 forms a valve seat for the diaphragm 70 of the bleed valve assembly. When the diaphragm 70 is lifted from the valve seat projection 66, the chamber formed by the recess 64 is in communication with a radially extending bleed vent passage 92 via a short axial passageway 94 extending through the center of the projection 66. As shown in FIG. 2, the bleed vent passage 92 is open to the ambient atmosphere external to the valve 10. As also shown in FIG. 2, the recess or space 72 above the bleed valve diaphragm 70 likewise communicates with the ambient environment through a port 96 having an entrance in the top surface of the lid section 16.

OPERATION OF THE INVENTION

The structure of the invention having been described in detail, its manner of operation will now be more easily understood. For the purposes of the following discussion, it will be assumed that the invention is used in connection with a medical ventilator; however, as previously mentioned, the invention's utility extends beyond this exemplary application.

Air from an air pump or compressor (not shown) is delivered, by suitable conduit means, to the inlet 30 in the base 12 of the valve body. A small amount of air from the chamber 22 enters the angled bore 56 and is delivered to the annular recess or space 34 on the upper side of the main diaphragm 42 via the bores 54, 58, and 60, and the restricted orifice 62. This sampled air will then flow through the bore 36 and the passageway 68 into the small upper chamber 64 which underlies the pilot valve diaphragm 70. At this point, the pressures in the chamber 22, the space 34, and the upper chamber 64 are equalized.

As previously discussed, the adjustment screw 86 is used to control the force applied by the pilot valve bias spring 82 to the pilot valve diaphragm 70 through the valve plate 78. Many medical ventilators are designed to operate most efficiently at a nominal pressure of approximately 11 PSI. In such a case, the tension of the spring 82 would be adjusted by means of the screw 86, so that the cracking pressure of the pilot or bleed valve is 11 PSI. Thus, if the pressure in the upper chamber 64 (which is the same as the pressure in the lower chamber 22) exceeds this value, the diaphragm 70 will be moved upwardly away from the valve stop 66, thereby allowing air to escape to the atmosphere through the bleed passage 94, 92. (It will be noted that the pilot or bleed valve cracking pressure will always be measured with respect to atmospheric pressure, since the space 72 above the lead valve diaphragm 70 is open to the ambient atmosphere via the vent port 96.)

As air is bled out of the bleed passage 94, 92, the pressure in the upper chamber 64 drops. Since the upper chamber 64 is in fluid communication with the annular space 34 above the main valve diaphragm 42 via the passageway 68, the pressure in the annular space 34 undergoes a corresponding drop. A pressure differential now exists across the main valve diaphragm 42, with the pressure above the diaphragm being less than the pressure 22 below the diaphragm. This pressure differential causes the diaphragm 42 to move upwardly away from its seat atop the cylindrical projection 24, so that air can escape through the axial bore 26 and the exhaust port 28. Thus, the pressure in the lower chamber 22 will be stabilized at substantially the same pressure as that of the upper chamber 64, which, in turn, is held at the nominal regulated value by means of the bleed or pilot valve assembly.

As previously discussed, to avoid significant deviations from the nominal value of the regulated pressure, it is necessary to minimize the amount of travel (in this case, compression) of the springs in the valve. With respect to the main valve spring 40, the spring constant is so small that the force exerted by the spring on the diaphragm 42 will be inconsequential regardless of the degree of spring compression. With regard to the bleed valve spring 82, however, the spring constant is large enough so that the compression-dependent force becomes a significant factor in its effect upon the nominal value of the regulated pressure. Therefore, the gas flow rate through the pilot or bleed valve should be minimized so that only minimal deflection of the diaphragm 70 is needed to achieve the bleeding function. It is to this end that the orifice 62 of the pressure sampling passage 50 is reduced in diameter, thereby restricting the flow rate from the lower chamber 22 into the upper chamber 64. While theoretically the diameter of the orifice 62 should be as small as possible, i.e., a pinhole, the diameter of orifice 62 cannot be made too small, lest the response time (i.e., the time needed to transmit a pressure change in the lower chamber 22 to the upper chamber 64) become too long. Thus, the diameter of the orifice 62 will reflect a compromise between fast response time and small deviations from the nominal value of the regulated pressure.

Optimally, in a pneumatic system such as used in a medical ventilator, the air compressor flow rate will always exceed the maximum expected demand. In such a situation, the flow rate from the compressor into the lower chamber 22 (which will be substantially constant) will always exceed the flow rate through the outlet 32, which reflects the patient's demand. Thus, any air that is not withdrawn from the outlet 32 by the patient would be discharged through the exhaust port 28, so that the flow rate through the inlet 30 would be approximately equal to the flow rate through the outlet 32 plus the flow rate through the exhaust vent 28 (the flow rate from the lower chamber 22 to the upper chamber 64 being so small as to be negligible by comparison).

From the foregoing, it can be appreciated that variations from the flow rate to the patient out of the outlet 32 will have a negligible effect upon the value of the output pressure regulated by the valve. This result is achieved since, as discussed above, the pilot valve is not subject to significant variations in flow rate, while the servo-type operation of the pilot valve allows the use of a main valve which is constructed so as to have negligible flow rate-dependent pressure characteristics, i.e., the use of a valve spring 40 which has only a minimal if not negligible spring constant. Thus, by way of specific example, with the adjustment screw 86 set for a nominal pressure of 11 PSI and air being delivered to the inlet from the compressor at 170 LPM, the flow rate to the patient can be varied from zero to approximately 120 LPM, with the pressure drop from the nominal value being as little as 0.3 to 0.5 PSI. By way of comparison, the use of a typical prior-art poppet-type relief valve would result in a change in outlet pressure, as flow rate to the patient increased from zero to 120 LPM, of about 1.0 to 1.5 PSI.

From the foregoing, it will be appreciated that the subject invention provides a significant improvement in precision and accuracy as compared with prior-art over-pressure relief valves, especially in situations where such valves are subjected to widely varying flow rates. Moreover, the invention is easily and economically constructed, requiring little or no high precision machining with the exception of the restricted diameter orifice 62.

Finally, since the regulated pressure is controlled by adjusting the tension on the pilot valve spring 82, which undergoes little deflection, calibration of the valve and control of the nominal value of the regulated pressure can be accomplished with a high degree of accuracy.

What is claimed is:

1. A gas pressure relief valve for maintaining the gas pressure in a pressurized gas system at a selected pressure, comprising:
   a first body section having a first face;
   a second body section having opposed second and third faces, said second face adjoining said first face and forming a first chamber therebetween;
   means in said first body section for providing an inlet to said first chamber for receiving pressurized gas and an outlet for conducting said gas to said system;
   an exhaust port in said first body section and communicating with said first chamber through a first valve seat, said first valve seat being approximately coplanar with the juncture between said first and second faces;
   a third body section having a fourth face adjoining said third face and forming a second chamber therebetween;
   a bleed vent in said second body section and communicating with said second chamber through a second valve seat, said second valve seat being approximately coplanar with the juncture between said third and fourth faces;
   main valving means, in said first chamber, for opening said exhaust port in response to the opening of said bleed vent and including a first pressure-responsive diaphragm captured between said first and second faces and engageable with said first valve seat;
   conduit means for communicating pressure between said first and second chambers; and
   pilot valving means, in said second chamber, and responsive to the pressure in said first chamber, for opening said bleed vent when the pressure in said second chamber exceeds said selected pressure, said pilot valving means including a second pressure-responsive diaphragm captured between said third and fourth faces and biased to close against said second valve seat with said selected pressure.

2. The gas pressure relief valve of claim 1, wherein said first diaphragm divides said first chamber into first and second portions, said first portion being within said first body section and said second portion being within said second body section.

3. The gas pressure relief valve of claim 2, wherein said conduit means comprises:
   a first conduit communicating between said first and second portions of said first chamber; and
   a second conduit communicating between said second chamber and said second portion of said first chamber.

4. The gas pressure relief valve of claim 3, further comprising:
   a restricted diameter portion in said first conduit.

5. The gas pressure relief valve of claim 1, wherein said main valving means further includes:
   resilient means for maintaining said first diaphragm in engagement with said first valve seat when the pressures on either side of said first diaphragm are approximately equal.

6. The gas pressure relief valve of claim 5, wherein said resilient means includes a spring having a negligible spring constant.

7. The gas pressure relief valve of claim 1, further comprising:
   means for adjusting the bias of said second diaphragm against said second valve seat.

8. The gas pressure relief valve of claim 1, wherein said bleed vent communicates directly between said second chamber and the atmosphere.

* * * * *